United States Patent [19]

Fischell et al.

[11] 4,440,160

[45] Apr. 3, 1984

[54] SELF-INJURIOUS BEHAVIOR INHIBITING SYSTEM

[75] Inventors: Robert E. Fischell; Glen H. Fountain; Charles M. Blackburn, all of Silver Spring, Md.

[73] Assignee: The Johns Hopkins University, Baltimore, Md.

[21] Appl. No.: 340,753

[22] Filed: Jan. 19, 1982

[51] Int. Cl.³ ............................................. A61N 1/38
[52] U.S. Cl. ............................. 128/132 R; 128/419 S
[58] Field of Search ................ 128/419 R, 419 S, 791, 128/802, 903, 731–733, 138 A, 782, 82.1, 132 R, 774; 340/407, 573; 361/232

[56] References Cited

U.S. PATENT DOCUMENTS

| 3,460,123 | 8/1969 | Bass | 128/138 A |
| 3,508,235 | 4/1970 | Baisden | 128/138 A |
| 3,834,379 | 9/1974 | Grant | 128/419 S X |
| 3,850,161 | 11/1974 | Liss | 128/419 S X |
| 3,885,576 | 5/1975 | Symmes | 128/802 X |
| 3,998,209 | 12/1976 | MacVaugh | 361/232 X |
| 4,048,986 | 9/1977 | Ott | 128/653 |
| 4,163,449 | 8/1979 | Regal | 340/573 X |
| 4,203,098 | 5/1980 | Muncheryan | 340/407 X |
| 4,292,630 | 9/1981 | Dumont | 340/573 |
| 4,359,724 | 11/1982 | Zimmerman et al. | 128/733 X |

FOREIGN PATENT DOCUMENTS 8101506 6/1981 Sweden ............................ 128/782

OTHER PUBLICATIONS

Friauf; "An Aversive Stimulator for Autistic Children;" *Medical and Biological Engineering;* vol. 11, No. 5, 9–1973, pp. 609–612.

*Primary Examiner*—Lee S. Cohen
*Assistant Examiner*—Angela D. Sykes
*Attorney, Agent, or Firm*—Robert E. Archibald; Howard W. Califano

[57] ABSTRACT

An apparatus for preventing self-injurious behavior in patients is disclosed. The apparatus generally contains one or more sensor modules, which detect self-injurious blows, and a separate stimulation module, which produces an aversive electric stimulation. The sensor module and stimulation module are mounted directly on a patient's body members, e.g., a sensor module can be mounted on a headband worn around the patient's head and the stimulation module can be mounted on an arm band worn around the patient's arm. The sensor module communicates with the stimulation module by either: (1) transmitting radio waves, which are received by the stimulation module or (2) sending a small alternating electrical signal through the patient's body, which is detected by electrodes in the stimulation module. In operation, a sensor module detects a blow to the sensed body member and sends a signal to the stimulation module which in turn generates a controlled electrical current for aversive stimulation.

8 Claims, 5 Drawing Figures

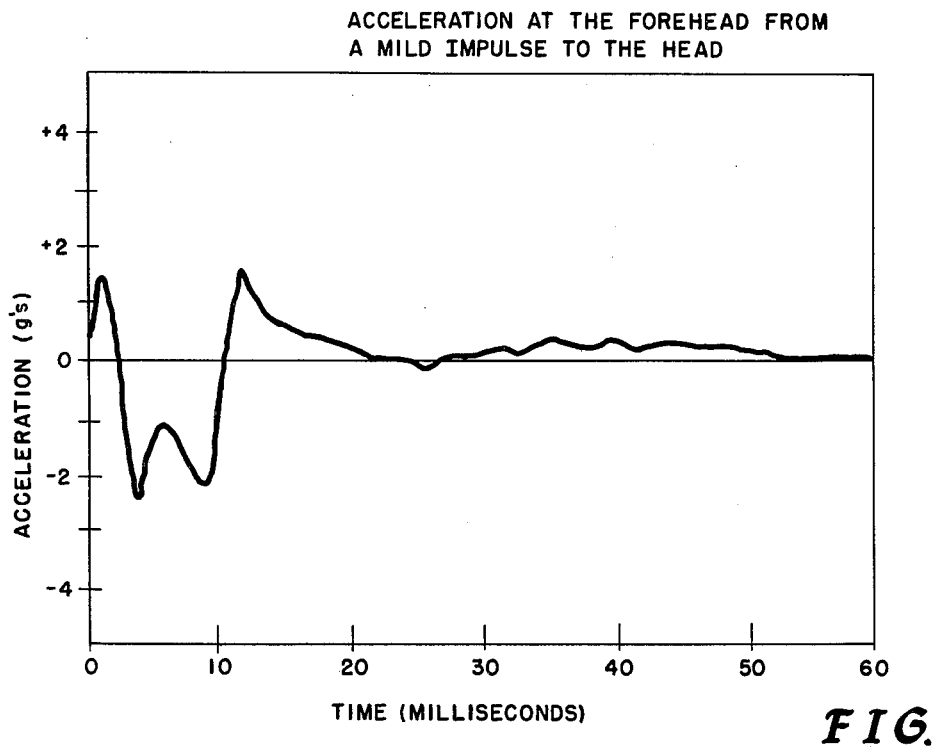
FIG. 3
ACCELERATION
| | |
|---|---|
| SUBWAY | 0.14g |
| AUTO | 0.2-.45g |
| MOTORCYCLE | 0.6g |
| COMMERICAL JET | 0.5 |
FIG. 4
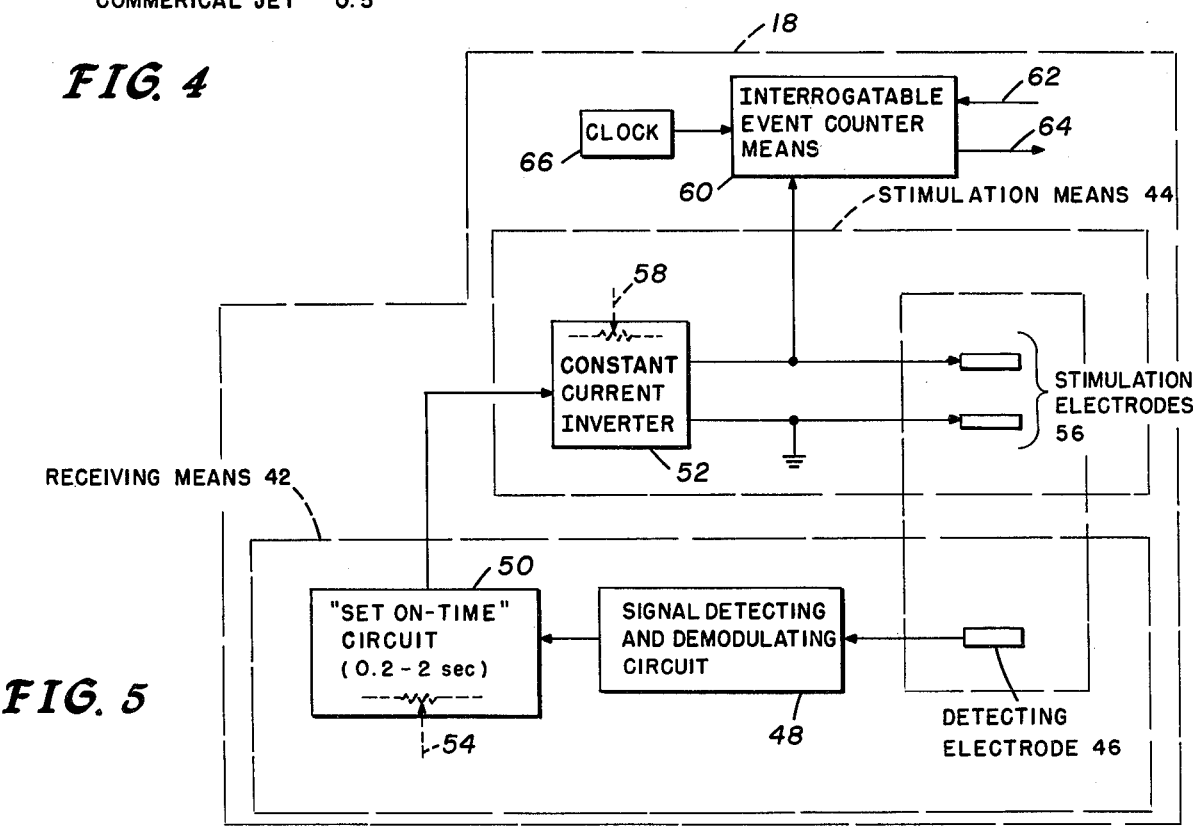
FIG. 5

SELF-INJURIOUS BEHAVIOR INHIBITING SYSTEM

BACKGROUND OF THE INVENTION

1. Field of the Invention

The invention relates to an apparatus for preventing self-injurious behavior in patients. More particularly, the invention teaches an improved apparatus for sensing self-injurious behavior and for transmitting a signal to a separate stimulation module which then supplies aversive electrical stimulation to the patient's skin.

2. Description of the Prior Art

The use of aversive stimulation to prevent certain types of behavior is known in the art. U.S. Pat. No. 3,998,209, issued to Gilbert Macvaugh on Dec. 21, 1976, teaches the application of electric shock pulses, generated by a charged capacitor circuit, for deconditioning snoring. U.S. Pat. No. 3,885,576, issued to Elliott Symmes, on May 27, 1975, teaches the use of electric shock as a means to deter smoking. In that patent a mercury switch is mounted on a wristband so that when the user moves his arm (e.g., to place a cigarette to his lips), the mercury switch closes and allows an electric current to flow to electrodes mounted on the user's wristband.

The use of aversive stimulation to inhibit self-injurious behavior was first described by Mooza Grant in U.S. Pat. No. 3,834,379, issued Sept. 10, 1974. Mooza Grant describes an apparatus which conditions psychotic self-destructive patients against self-injurious blows to the head. The apparatus contains a helmet which is mounted on the patient's head to absorb self-injurious blows. The helmet contains a metallic cylinder and a movable pin disposed centrally therein. When the patient strikes the helmet, the pin contacts with the cylinder and establishes an electrical contact which activates an electronic package (described as being disposed within a packet in patient's clothes.) An electrical pulse generated in the electronic package is sent to the electrodes contained in an arm band and provides an aversive electric shock to the patient's arm. The helmet, electronic package, and stimulation electrodes are all connected by electrical wires.

SUMMARY OF THE INVENTION

The prior art apparatus required bulky equipment and connecting cables which run between the sensing transducer, and the stimulation circuitry and electrodes. Observations of patients indicated that the connecting wires restricted the patient's activities. The invented apparatus contains a sensor module that is separate from the stimulation module and provides a wireless communication link between the sensor and stimulation modules.

The prior art aversive stimulation apparatus required a bulky helmet to support the sensing switch and also to protect the head. For the sensor module, the proposed apparatus of the present invention uses a miniature accelerometer and electrical circuitry which is contained in a single miniaturized hybrid circuit, all of which can be mounted on an elastic headband. The invented apparatus enables the patient to be conditioned against self-injurious behavior without requiring the patient to wear a bulky helmet which inhibits his or her activities, which can be uncomfortable when worn for extended time periods, and which causes the patient to have an abnormal appearance.

The inventors also observed that patients exhibiting such self-injurious behavior frequently injure body members other than the head. The present invention thus discloses a sensor module which can be attached to an elastic band and worn on any body member. Moreover, several of the invented sensor modules can be worn on different body members and can simultaneously communicate with a single stimulation module, and report an injurious blow to any of the sensed body members. Not only does the prior art not teach the use of multiple sensors but, the interconnection cables used in the prior art would entangle the patient in a web of wires if such sensing from multiple locations was attempted. Typical of other body members where sensing might be useful are elbows and knees.

The present invention uses a separate sensor and stimulation module, each made from a hybrid circuit containing (CMOS) integrated circuits. The sensor module detects a rapid acceleration or blow and transmits a signal to a remote stimulation module. The sensor module might be mounted on the body member that is being struck or on the body member that is doing the striking. In either case, it is to be understood that a body member is being struck. The transmission made by the sensor module can be by means of radio emissions (i.e., electromagnetic waves) or by a unique method of transmitting an electrical signal through the patient's body. The stimulation module detects and demodulates the transmitter signal and provides aversive stimulation in response to each detected self-injurious action. Aversive stimulation is provided by means of stimulation electrodes which are placed in contact with the patient's skin. In operation, each sensor module can detect self-injurious blows to a particular body member and communicate this information to the stimulation module which then provides an aversive electrical shock.

One novel feature of the invented apparatus is the use of a sensor module which is remote from and not connected by wires to the stimulation module.

The second novel feature of the invented apparatus is the use of a wireless communication link between the sensor and stimulation modules.

A third novel feature of the invented apparatus is the ability of the sensor module to transmit an electrical signal containing event information through the patient's body, and to have the transmitted signal be detected and be demodulated by the stimulation module.

A fourth novel feature of the invented apparatus is to mount the sensor module on an elastic band. As such, the sensor module can be worn as a headband (not a bulky helmet) to detect self-injurious blows to the head, and it can be worn on an arm or knee band to detect self-injurious behavior to the arm or leg respectively.

A fifth novel feature of the invented apparatus is that one or more sensor modules can simultaneously communicate with a single stimulation module. This feature allows the invented apparatus to be successfully used for patients who exhibit self-injurious behavior to more than one body member.

A sixth novel feature of the invented apparatus is the incorporation of a recording means in both the stimulation and sensor modules. This feature allows the invented apparatus to be a more useful diagnostic tool.

A seventh novel feature of the invented apparatus is an aversive stimulation system where the level of the electrical shock is adjustable to provide a minimum shock level that will accomplish the intended purpose.

BRIEF DESCRIPTION OF THE DRAWINGS

FIG. 3 is a graph showing acceleration versus time for acceleration at the forehead caused by a mild blow to the head.

FIG. 4 is a table showing various accelerations a patient will experience during normal activities.

FIG. 5 is a block diagram of the stimulation module.

DETAILED DESCRIPTION OF THE PREFERRED EMBODIMENT

Figure 1:
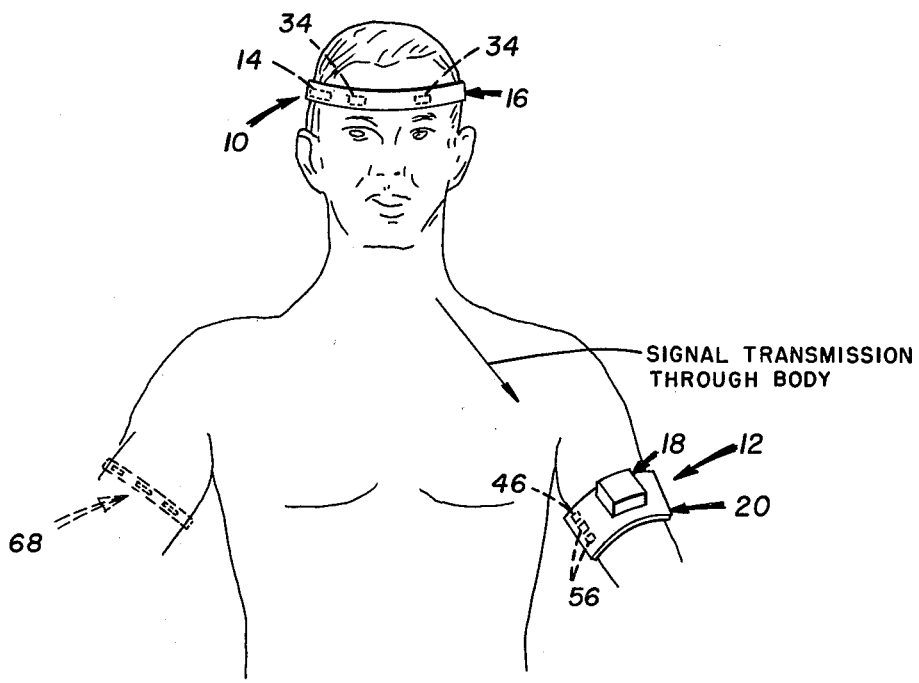
FIG. 1 is an illustration of a person wearing the invented self-injurious behavior inhibiting system.
Figure 2:
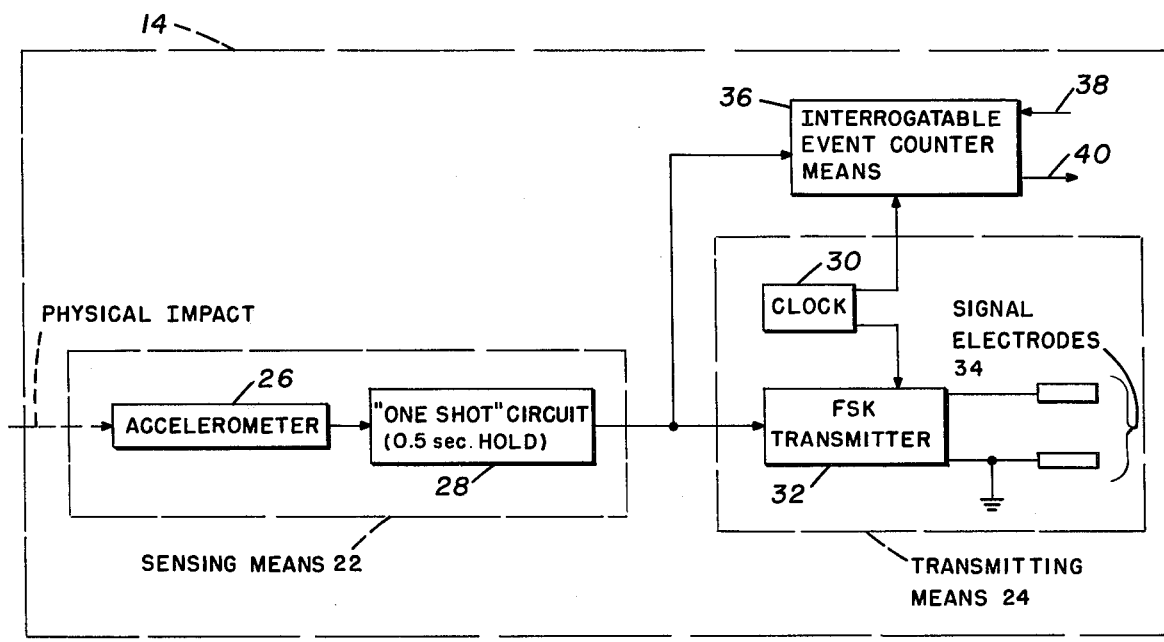
FIG. 2 is a block diagram of the sensor module.

The proposed apparatus for inhibiting self-injurious behavior is illustrated in FIG. 1. The apparatus is generally composed of a sensor module subsystem 10 and a separate stimulation module subsystem 12. The sensor module subsystem 10 contains a sensor module 14 which is mounted on a headband 16 and detects blows to the patient's head. Although not illustrated in FIG. 1, the sensor module 14 could also be mounted on any other body member and detect blows to that body member (e.g., sensor modules could be mounted on an elastic elbow band, knee band, ankle band, wristband, etc.). For patients who exhibit injurious behavior to several different body members, it is within the scope of this invention to place sensor modules on several body members simultaneously, and to detect self-injurious blows to each of those body members. Furthermore, if the patient always uses his hand to strike a variety of body parts, then a sensor module mounted on his wrist could detect any body part being hit by his hand and this would cause an appropriate signal to be sent to the stimulation module. The stimulation module subsystem 12 is mounted on the patient's body at a position remote from the sensor module subsystem 10. The stimulation module subsystem 12 consists of a stimulation module 18 mounted on an elastic band 20. FIG. 2 shows the stimulation module subsystem 12 mounted on the patient's arm, although the stimulation module subsystem 12 could be mounted on other body members depending on its effectiveness for a particular patient.

Unlike the prior art, the invented apparatus contains no wires or cables connecting the sensor module 14 to the stimulation module 18. As will be described in greater detail, the sensor module 14 transmits a signal either through the body or by propagated radio waves to the stimulation module 18. The signal transmitted by the sensor module 14 carries event information which indicates when a blow has been sustained. The stimulation module 18 applies aversive stimulation to the patient in response to this event information. It is contemplated that several sensor modules mounted on different body members can transmit event information to a single stimulation module.

FIG. 2 is a block diagram of the sensor module 14. The sensor module would generally consist of a single hybrid circuit typically consisting of (CMOS) integrated circuit components chosen for their low voltage requirements, and particularly because of their low electrical power drain. The sensor module 14 contains a sensing means 22 for sensing a blow to a body member, and a transmitting means 24 for transmitting a signal to the stimulation module 18. The sensing means 14 further contains: a miniaturized two-axis or three-axis accelerometer 26; a small single cell battery (not shown), such as a Li $So_2Cl$ battery; and, a "one-shot" circuit 28. The accelerometer 26 behaves as a switch and is closed momentarily when an accelerating impulse, above a set threshold level, is detected, and automatically resets after the acceleration impulse subsides. FIG. 3 contains a graph showing acceleration detected at the forehead of a person experiencing a mild blow to the head. A 2 g acceleration level is attained with a slight, non-damaging impulse to the head. A typical self-injurious blow might produce a 20 g acceleration to the head or other body member. A threshold level between 2 g's and 5 g's can be selected as values large enough to avoid aversive stimulation as a result of accelerations experienced in normal activity, and yet small enough to detect even a non-damaging impulse to the head. FIG. 4 contains a table showing some accelerations experienced in normal activities particularly in various types of transportation—(the threshold value is chosen so that acceleration experienced during transportation would not activate the invented apparatus.)

Although the use of an accelerometer switch is described herein, the sensor module could also use the actual blow to cause electrical contact between two surfaces or the blow might be detected by a change in capacitance caused by the proximity of two body members coming in contact.

Returning now to FIG. 2, a "one-shot" circuit 28, or its equivalent, is connected to the accelerometer 26 and will be activated when the accelerometer output exceeds a threshold level for a period longer than 10 milliseconds. (NOTE: A range of threshold values, other than those specified above, is contemplated by the inventors—any threshold value is acceptable which would be large enough to avoid stimulation during normal activity but sensitive enough to detect mild non-injurious blows.) The "one-shot" circuit 28 shall not accept another input from the accelerometer for the duration of a hold period (a hold period of 0.5 seconds is suggested). The "one-shot" circuit 28 sustains a level output during the hold period enabling the "one-shot" circuit 28 to "stretch" the electrical impulse received from the accelerometer 26 thus allowing the transmitting means 24 time to (1) be powered, (2) to be stabilized, and (3) to transmit a signal indicating the occurrence of the self-injurious blow.

The transmitting means 24 has two embodiments. In the first embodiment, the transmitter means 24, as shown in FIG. 2, contains a crystal oscillator clock 30 and an FSK transmitter 32, which generates FSK frequencies of 48 kHz (a logical "0") and 52 kHz (a logical "1"). The FSK transmitter 32 is of a design known in the communication art and will produce a [coded] signal at a 5-millisecond bit rate. The transmitter 32 is activated by the "one-shot" circuit 28 and, after it stabilizes, transmits a signal for the remainder of the 0.5 second hold period. The output signal from the transmitter 32 runs to signal electrodes 34 (also see FIG. 1) which are in contact with the patient's skin and electrically couple the transmitter 32 output to the patient's body. The electrical signal, generated by the FSK transmitter 32, is conducted by electrodes 34 to the patient's skin and travels through the patient's body to be received by a remotely located stimulation module 18. It should be noted that any type of alternating electrical signal can be conducted through the human body in the manner disclosed above. This technique is more fully described in co-pending U.S. application entitled "Intracorporeal and/or Extracorporeal Biomedical Device Systems Having Two or More Modules," invented by R. E. Fischell, filed of even date herewith, and incorporated by reference. The present inventors contemplate the use of a transmitter in which an appropriate frequency carrier could be modulated, in any manner known in the art, to produce the desired communication signal.

In the second embodiment, not shown in FIG. 2, the transmitting means 24 emits RF electromagnetic radiation through an antenna. At least some of the electromagnetic radiation is propagated outside of the body and is received by an RF receiver contained in the stimulation module. An RF transmitter and receiver as described above, are of a design known in the communication art.

The sensor module 14 may contain an interrogatable event counter means 36 for diagnostic purposes. The event counter means 36, shown in FIG. 2, obtains its input from the "one-shot" circuit 28 and thus counts the occurrence of each self-injurious blow. The event counter means 36 obtains a timing input from the clock 30 and the time of occurrence of each self-injurious blow is also recorded. An interrogatable input line 38 from an external monitoring device (not shown) can cause the data recorded in the event counter means to be read out on line 40 into such an external monitoring device. Alternatively, the event counter means 36 itself, might have displayed on it (e.g., by an LED display) the data relative to numbers and time of occurrence of acceleration events.

In the apparatus illustrated in FIG. 1, the sensing module 14, and signal electrodes 34, are mounted on an elastic headband 16. The signal electrodes 34 are located on the inner surface of the elastic band 16 and make electrical contact with the patient's skin.

It is also within the contemplation of this invention to mount the sensor module 14 in a protective means mounted on the patient's head which shields the patient's head from self-injurious blows. When the sensor module is mounted in such a protective means, conducting electrodes are placed on the inner surface of the protecting means so as to make good electrical contact with the patient's skin.

FIG. 5 is a block diagram showing the stimulation module 18. Stimulation module 18 is made from a hybrid circuit containing (CMOS) integrated circuits chosen for their low voltage requirement and low electric power drain. The stimulation module 18 consists of a receiving means 42 and a stimulation means 44. The receiving means 42 has two preferred embodiments. The first embodiment (shown in FIG. 5) receives and demodulates electrical signals sent through the patient's body. This embodiment contains: a detector electrode 46, a signal detection and demodulation circuit 48, a "set on-time" circuit 50, or its equivalent, and a battery (not shown). The detecting and modulation circuit 48 is of a typical design known in the communication art. The electrical signal is picked up by the detecting electrode 46 which is placed in contact with the patient's skin. The detecting electrode 46 connects to the detecting and demodulation circuit 48 which demodulates the electrical signal. When the event information indicates that self-injurious action has occurred, the "set-on time" circuit 50 is triggered. Once the "set-on time" circuit 50 is triggered, power is supplied to the constant current inverter 52 for a set period of time. This set period of time defines the length of the aversive stimulation and is controlled by adjusting potentiometer 54 in the "set-on time" circuit 50. It is recommended that the "on-time" be adjusted between 0.2 and 2.0 seconds.

The second embodiment of the receiving means (not shown in FIG. 5) includes a small antenna and a miniaturized radio receiver tuned to the frequency transmitted by the radio transmitter in the sensor module. The receiver is of a typical design known in the communication art. The detected signal is demodulated and the "set-on time" circuit 50 is triggered, as described above.

The stimulation means 44, shown in FIG. 5, consists of a constant current inverter 52 and stimulation electrodes 56. The current is supplied to the constant current inverter 52 from the "set-on time" circuit 50 as described previously. The constant current inverter 52 delivers a current to the stimulation electrodes 56, which are held in contact with the patient's skin. The constant current inverter 52 should be set to deliver stimulation current in a range from 1 to 100 milliamperes, and the frequency of stimulation should be adjustable. The potentiometer 58 on the constant current inverter 52 allows the amplitude of the aversive stimulation to be adjusted to a minimum value that accomplishes the intended purpose of deterring self-injurious behavior.

As shown in FIG. 1, the stimulation module 18 can be mounted on an elastic arm band 20. The stimulation electrodes 56, and the detecting electrode 46 are placed on the inside surface of the arm band so as to make contact with the patient's skin. The stimulation module may alternatively be mounted on other body members and may alternatively be mounted by means other than an elastic band.

As illustrated in FIG. 5, an interrogatable event counter means 60 is connected to the output of the constant current inverter 52. The event counter means 60 provides a record of the number of times that the constant current inverter 52 was activated. The event counter means in 60 is similar in design function and use to the event counter means 36 associated with the sensor module 14 of FIG. 2. The event counter means 36 includes the use of line 62 to initiate interrogation and line 64 for data readout into an external monitoring device (which is not shown). A clock 66 provides timing input for the event counter 66 so that the relative time of each aversive stimulation can be recorded.

In operation, one or more sensor modules would be worn by the patient. Any impact to a sensed body member (which sensed member might include the part of the body that is doing the striking) causing an acceleration greater than 2 g's for a duration of 1.0 millisecond will be sensed as a self-injurious event. The transmitting means 24 included in the sensor module 14 will transmit a signal to a remotely placed simulation module 18. Two embodiments have been described for the transmitter means. In one embodiment the signal containing event information is transmitted through the body. In the other embodiment the signal is transmitted by conventional radio propagation. The stimulation module 18 is mounted on a different body member from the sensor module 14 and contains a receiving means 42 which detects and demodulates the signal transmitted from the sensor module 14. There are two possible embodiments of the receiver means. In one embodiment the receiver detects an electric signal transmitted through the body. In the other embodiment the receiver recovers signals transmitted by conventional radio propagation. The receiving means 42 detects and demodulates the signal.

With the occurrence of self-injurious behavior, the "set-on time" circuit 50 is activated. The "set-on time" circuit 50 in turn powers the constant current inverter 52 which supplies an alternating electric current to the patient's body through the stimulation electrodes 56, which are in contact with the patient's skin. The potentiometers 54, and 58, allow the duration and amplitude respectively of the aversive electrical current to be adjusted. In this manner, an aversive stimulation is supplied to a remote portion of the patient's body in response to a blow sustained by the head or other body member.

In another embodiment, a plurality of sensor modules can be mounted on other body members to detect injurious impacts to those body members or delivered by a particular body member. For illustration, FIG. 1 shows a sensor module 14 mounted on the patient's head and also a sensor module 68 mounted on the patient's right arm. Both sensor modules 14 and 68 are worn simultaneously and communicate to the stimulation module 20 subsystem 12. Sensor modules can simultaneously be placed on the patient's head, arms, legs, elbows or knees, or other body parts depending on the form of injurious behavior a particular patient exhibits.

Obviously many modifications and variations of the present invention are possible in light of the above teachings. It is therefore to be understood that, within the scope of the appended claims, the invention may be practiced otherwise than as specifically described.

What is claimed and desired to be secured by U.S. Patent is:

1. An apparatus for inhibiting self-injurious behavior, comprising:
   at least one sensor module, adapted to be mounted on any of patient's body members, each of said at least one sensor module being mounted on a different body member, and each of said at least one sensor module including,
   (a) an accelerometer which detects an acceleration due to a physical impact of said body member,
   (b) a "one-shot" circuit connected to and activated by said accelerometer to produce a constant signal for a set period of time,
   (c) a clock which provides timing pulses,
   (d) a transmitter, connected to and activated by said "one-shot" circuit, which receives timing pulses from said clock and produces an electromagnetic signal,
   (e) an interrogatable event counter, connected to said clock and said "one-shot" circuit, to count and record the number of physical impacts; and,
   a stimulation module, adapted to be mounted on said patient's body at a location remote from said at least one sensor module, communicating by a wireless link to said at least one sensor module, said stimulation module including,
   (a) a signal detecting and demodulating circuit, which provides a triggering signal after detecting and identifying said electromagnetic signal,
   (b) a "set-on time" circuit, connected to and actuated by said signal detecting and demodulating circuit, which sets the time period of stimulation,
   (c) a means connected to and activated by said "set-on time" circuit, for generating an aversive electric current,
   (d) stimulation electrodes, connected to said means for generating an aversive electric current, which conduct said aversive electric current to the skin of said patient's body,
   (e) a clock to provide timing pulses, and
   (f) an interrogatable event counter, connected to said clock and said means for generating an aversive electric current, to count and record the number of times said aversive electric current is generated.

2. The apparatus of claim 1 wherein said accelerometer is adjustable to detect an acceleration impulse above a certain threshold, said threshold being set to distinguish acceleration due to normal activity from acceleration due to self-injurious behavior.

3. The apparatus of claim 2, wherein said threshold is set to a value of 2 g.

4. The apparatus of claim 1, wherein said accelerometer is a two-axis accelerometer.

5. The apparatus of claim 1, wherein said accelerometer is a three-axis accelerometer.

6. The apparatus of claim 1, wherein said stimulation module is mounted on a band which is adapted to snugly encompass a body member.

7. The apparatus of claim 1, wherein each of said at least one sensor module is mounted on a band which is adapted to snugly encompass a body member.

8. The apparatus of claim 1, wherein one of said at least one sensor module is mounted in a protective helmet adapted to be mounted on the head of said patient.

* * * * *